United States Patent
Rozsa et al.

[11] 3,966,786
[45] June 29, 1976

[54] METHOD FOR PRODUCING CHLOROFORMATES

[75] Inventors: Laszlo Rozsa, Miskolc; Lajos Meszaros, Szeged; Ferenc Mogyorodi, Miskolc, all of Hungary

[73] Assignee: Eszakmagyarorszagi Vegyimuvek, Sajobabony, Hungary

[22] Filed: Jan. 28, 1972

[21] Appl. No.: 221,504

[52] U.S. Cl. .................................. 260/463; 23/260
[51] Int. Cl.² .......................................... C07C 68/02
[58] Field of Search ............................... 260/463

[56] References Cited
UNITED STATES PATENTS

| | | | |
|---|---|---|---|
| 2,337,172 | 12/1943 | Wojcik | 260/463 |
| 3,646,102 | 2/1972 | Kobayashi et al. | 260/463 |

FOREIGN PATENTS OR APPLICATIONS

| | | |
|---|---|---|
| 1,217,012 | 4/1960 | France |

OTHER PUBLICATIONS
Saunders et al., J. Am. Chem. Soc., 73 3796–3797 (1951).

*Primary Examiner*—Nicholas S. Rizzo
*Assistant Examiner*—Diana G. Rivers

[57] ABSTRACT

Various chloroformates are produced from aliphatic, substituted aliphatic, cycloaliphatic, aromatic and arylaliphatic alcohols having up to 20 carbon atoms and of phosgene in a continuous, concurrent flow process, with the alcohol starting material being atomized into the reactor, whereby the reaction takes place largely in the fog phase. The vapor pressure of the phosgene can be utilized for the creation of the fog phase and the termination of the atomized state can be used for efficiently separating the chloroformate end product from the hydrogen chloride by product. The process can be carried out in a reactor comprising a reaction zone, a charged zone and a zone for the recovery of the end product.

13 Claims, 1 Drawing Figure

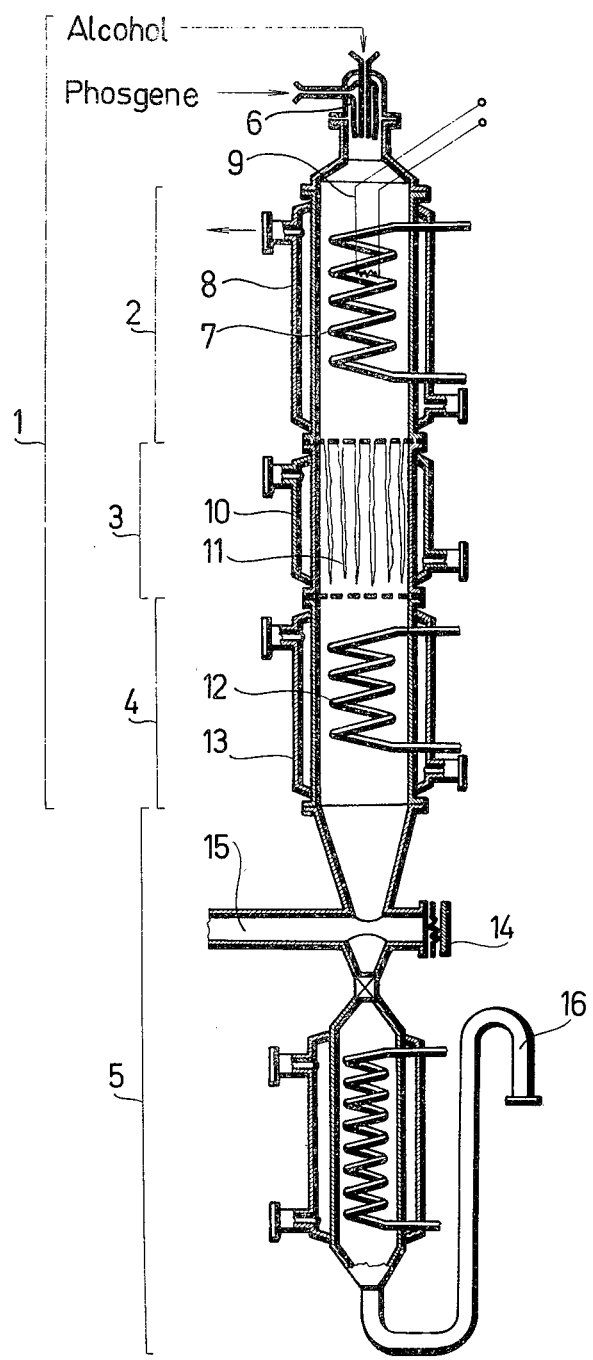

METHOD FOR PRODUCING CHLOROFORMATES

The present invention relates to the production of chloroformates, more particularly, the present invention relates to the continuous production of chloroformates having a high purity, by the reaction of an alcohol and phosgene, in a process having a high yield.

Various chloroformates are widely employed in a large number of applications in the chemical and pharmaceutical industries. For example, various carbamates can be produced by the reaction of a chloroformate with an amine. It is well known in the art to produce chloroformates by the reaction of an alcohol and phosgene (e.g. Beilstein, Handbuch der Organischen Chemie, 4th Edition, third volume, part 1, pages 23–30). During the reaction hydrogen chloride is formed in a generally relatively highly exothermic reaction. In many instances, especially in the case of lower carbon atom-containing aliphatic alcohols, the reaction continues in a manner in which a part of the alcohol is converted into a dialkyl carbonate, while also some of the alcohol is consumed in the reaction with the hydrogen chloride and thus less alcohol remains available for reaction with phosgene.

Some prior art processes attempted to eliminate the undesirable side reactions by using a large stoichiometric excess of phosgene and by conducting the reaction while cooling the reaction zone to a low temperature such as between 0° and 10°C, i.e. a temperature at which the excess phosgene remains in solution and at which the rate of ester formation is still acceptable. In these prior art processes the alcohol is added to the phosgene which is in the liquid phase, while the temperature of the reaction zone is maintained by cooling at about 0°C, and while stirring the reaction mixture, to maintain an excess of phosgene. Subsequently the reaction mass is allowed to heat up and the excess phosgene is removed by flushing with nitrogen, and the resulting crude chloroformate is purified by vacuum distillation. In some cases the alcohol is not added to liquid phosgene, but to a saturated solution of phosgene in an organic solvent such as toluene or benzene, to increase the heat capacity of the reaction mass. In the latter case first the crude chloroformate has to be separated from the solvent by distillation, before the pure chloroformate end product can be recovered.

These prior art methods are usually carried out in lead-lined or enameled autoclaves provided with reflux condensers, cooling jackets and stirrers. In the more modern installations several autoclaves are employed in a series cascade system.

The prior art industrial scale methods for the production of chloroformates have several disadvantages. These include the fact that they are carried out necessarily batchwise, requiring installations of large volume and large cooling capacity for the liquefaction of phosgene and for the cooling of the reaction mass. Furthermore, special costly construction materials are necessitated by the corrosive character of the end product and of the hydrogen chloride by product. The resulting crude product usually contains a high proportion of hydrogen chloride and carbonate impurities which can generally be removed from the chloroformate only by vacuum distillation. Another disadvantage of the prior art processes is that at any given time the reaction vessel contains a large amount of highly toxic phosgene which represents a dangerous condition in the case of equipment failure. Due to the presence of corrosive materials equipment failure occurs rather often in prior art processes.

A somewhat improved prior art process is disclosed in French Pat. No. 1,336,606. The reaction between alcohol and phosgene is carried out in a charged column under countercurrent flow conditions. Alcohol is fed in at the top of the column and it trickles downward as it contacts the upward stream of gaseous phosgene which is introduced at the bottom of the column. Due to the heat of reaction, an upwardly increasing temperature gradient is formed in the reactor column. For example, in the case of the preparation of ethyl chloroformate, if the starting ingredients are fed into the system at 200°C, the heat of reaction will cause the reaction zone to heat to about 50°C which further upwardly in the column increases to about 74°C. The reaction mixture which is continuously recovered at the bottom of the column contains, in addition to the chloroformate, also considerable amounts of alcohol, dialkyl carbonates and hydrogen chloride. The latter, for example, is typically present in a concentration of about 12%. In accordance with the process of the French patent, esterification has to be accomplished at temperatures below the boiling point of the alcohol.

A similar process is described in U.S. Pat. No. 2,778,846 wherein chloroformates are prepared at temperatures that are below the temperature at which carbonate formation occurs. Hydrogen chloride is separated from the chloroformate by removal at various points of the system and the temperature of the chloroformate is maintained higher at the point of separation than the temperature of the hydrogen chloride. Here also the reaction is carried out continuously in a countercurrent.

It is a common feature of both of these prior art processes that the alcohol which trickles downward in the column meets with the upward moving gaseous phosgene at the interface of these two phases. At this time heat is given off, resulting in an increasing gradient in the apparatus, while hydrogen chloride is formed in the reaction of the alcohol and phosgene. The hydrogen chloride then moves upward with the phosgene, reacts further with the alcohol to form an alkyl chloride and water. The latter can hydrolyze the chloroformate, thus further reducing the yield of these prior art processes.

A common drawback of these prior art processes is the formation of the temperature gradient in the reactor, which makes the conduct and control of the reaction exceedingly difficult. The ingredients of the reaction are constantly contacted by the hydrogen chloride by-product of the reaction, thus reducing the efficiency of the process and resulting in a contaminated end product. A further drawback of the last two prior art processes is that they are suitable only for the production of chloroformates of relatively low number (1 – 5) of carbon atoms in the molecule.

In accordance with the present invention, it was discovered that chloroformates of desirably high purity can be produced with good yields from aliphatic, substituted aliphatic, cycloaliphatic, aromatic and arylaliphatic alcohols having up to 20 carbon atoms, by their reaction with phosgene, in a concurrent, continuous flow, if the reaction is carried out with the alcohol component being atomized into a fog, under isothermic circumstances. The vapor pressure of the phosgene can be utilised for the creation of the atomized state. After the reaction is carried out in the atomized state, the hydrogen chloride and the chloroformate can be efficiently separated from each other by terminating the atomized state in an otherwise known manner.

One can prevent the hydrogen chloride from contacting the alcohol and immediately entering into a reaction therewith, by utilizing the vapor tension of the phosgene to create the atomized state. During the course of the reaction in the atomized state, part of the heat of the reaction is used to increase the degree of dispersion and thus isothermic circumstances are created in all parts of the reaction zone, and no temperature gradients will occur. As a result of the isothermic circumstances the kinematic balance of the reaction shifts substantially towards the forward direction of the reaction equation, the reaction takes place substantially instantaneously and insignificant amounts of by product (carbonate) is formed. It has been surprisingly found that practically identically good yields and purity of chloroformates can be obtained regardless of whether the reaction is carried out under the isothermic circumstances created by the heat of reaction or by the use of additional heating, at elevated temperature above the temperature of carbonate formation or above the boiling point of the alcohol. The process of the present invention is equally suitable for the preparation of aliphatic, substituted aliphatic, cycloaliphatic, aromatic and arylaliphatic chloroformates having up to 20 carbon atoms in the molecule and, up to this limit the length of the aliphatic chain and the number of carbon atoms therein does not limit the utility of the process of the present invention, as contrasted to the much more stringent limitations of the prior art processes.

The present invention is disclosed further in greater detail, with reference being had to the accompanying drawing the single FIGURE of which illustrates an embodiment of the apparatus of the present invention.

The apparatus includes a vertical columnar reactor 1 which is divided into three zones: (a) a reaction zone 2, (b) a charged zone 3, and (c) a condensation zone 4. The reaction products can be removed from the reactor 1 through a removal zone 5. Alcohol and phosgene are introduced into the reaction zone 2 through a nebulizer 6. The reaction zone 2 can be suitably heated by an internal heating coil 7 and a heating jacket 8, while actinic or any other desirable activating energy can be added by an ultraviolet or other light source 9.

The charged zone 3 is provided with a heating jacket 10, and a charge 11 having a large specific surface, such as glass wool. The condensation zone 4 can be suitably cooled by its inner cooling coil 12 and cooling jacket 13.

The removal zone 5 includes a pulsing device 14 such as a positive displacement pump or a membrane pump or similar device to provide alternatingly increasing and decreasing pressure pulses for reducing the throughput time of the reactor 1. The removal zone 5 further includes an outlet 15 for the removal of hydrogen chloride and a cooled outlet 16 for the removal of the chloroformate end product.

In the production of chloroformates the alcohol and phosgene starting ingredients are introduced into the column 1 through the atomizer 6 where the atomized alcohol particles are formed with the aid of the vapor pressure of the phosgene in an otherwise known manner. In the reaction zone 2 the reaction between the alcohol and phosgene takes place substantially instantaneously and the heat which evolves during the reaction creates isothermic conditions throughout the zone. The reaction takes place in the reaction zone under isothermic circumstances even if it is conducted at an elevated temperature such as by the introduction of heat by the heating coil 7 and/or the jacket 8, or if activating energy for starting the reaction is provided by the light source 9.

After the reaction has taken place instantaneously in the zone 2, the reaction products are recovered in the charged zone 3 and the condensation zone 4 either by directly terminating the atomized state or by converting it into vapor phase and then condensing the chloroformate end product. The heat which evolves during condensation increases the heat content of the hydrogen chloride and prevents its dissolution in the chloroformate.

The cooling surfaces 12 and 13 of the condensation zone 4 can be used to regulate the temperature of the chloroformate so that when it reaches the removal zone 5 its temperature should be between 30° and 60°C, suitably between 35° and 45°C. The hydrogen chloride is led away through the pipe 15 together with any small amounts of unreacted, possibly stoichiometric excess, of phosgene, while the chloroformate is recovered through the pipe 16 in which it is suitably further cooled to allow any amounts of unreacted alcohol to be removed by later washing.

The very short throughput times of the apparatus in accordance with the present invention allow good productivity when the starting ingredients are continuously introduced at one end and the finished chloroformate is continuously recovered at the other. The advantage of short throughput times and of continuous operation is that a reaction vessel of small size and low cost can be used, even if made from glass or other relatively expensive structural material which can withstand the corrosive characteristics of the chloroformate. Another advantage of the short throughput times is that at any given time relatively small amounts of material are in the reactor, and even of these small amounts of material phosgene constitutes only a small proportion and since it immediately reacts with the alcohol in the reaction zone only any stoichiometric excess which may have been employed is present in the free state. Therefore, if any malfunction of apparatus or accident occurs, the amount of phosgene which can escape is only very small.

The present invention is further disclosed by way of specific illustrative examples thereof, setting forth the best mode contemplated for carrying out the invention. A glass reactor of 1,800 mm length and 100 mm diameter is used and a throughput time of from about 10 to about 20 seconds is obtained. Yields, based on phosgene, of 96–98% are obtained throughout.

EXAMPLE 1

370.5 grams methanol and 1,100 grams phosgene are added hourly to the reactor. A temperature of 64°C develops in the reaction zone. At the bottom of the reactor 1,012.7 grams per hour of raw product are obtained, containing 962.7 grams methylchloroformate. The yield based on the alcohol is 88% and the yield based on phosgene is 96%. The throughput time is 13 seconds.

EXAMPLE 2

Each hour 521.5 grams ethanol are atomized into the reactor with the aid of 1,100 grams of phosgene of the reaction zone is adjusted by heating, to 120°C. With a throughput time of 14 seconds, hourly 1,215.9 grams raw product are recovered, which contains 1,127.9 grams ethyl chloroformate. The yield of the reaction is 92% based on the ethanol and 98% based on the phosgene.

EXAMPLE 3

With the aid of 1,100 grams phosgene per hour, 696.5 grams isopropanol are atomized each hour into the reaction zone where a temperature of 60°C is obtained. With a throughput time of 16 seconds, 1,329.4 grams of raw product are obtained each hour, containing 1,274.4 grams isopropyl chloroformate. The yield based on the alcohol is 90% and based on phosgene is 96%.

EXAMPLE 4

530 grams per hour of phosgene are utililized to atomize each hour a solution of 1,000 grams cetol in 2,000 ml benzene. The reaction zone adjusts at a temperature of 39°C. Cetyl chloroformate is distilled off from the resulting benzene solution, resulting in an end product of 1,170 grams, which corresponds to a yield, based on cetol, of 80%.

EXAMPLE 5

A feed of 455 grams ethylene chlorohydrin per hour is atomized into the reactor with the aid of 563 grams per hour of phosgene. A temperature of 36°C adjusts itself in the reaction zone and 934 grams of 94% pure 2-chloroethyl chloroformate are obtained.

When additional heating is used to obtain 60°C in the reaction zone, 944 grams of raw product are obtained; at 80°C 955 grams raw product, and at 100°C in the reaction zone the hourly output of the raw product is 955 grams. This corresponds to a yield, based on ethylene chlorohydrin, of 92%.

EXAMPLE 6

232.8 grams per hour phosgene are utilized to atomize 270.6 grams per hour β-butoxyethanol into the reaction zone. Without any additional heat the exotherm reaction provides a reaction zone temperature of 66°–68°C. With a 15 second throughput time 472 grams per hour raw end product are obtained which contains 95% β-butoxyethyl chloroformate. The yield, based on the starting alcohol, is 92%.

EXAMPLE 7

An hourly feed of 600 grams cyclohexanol and 623.2 grams phosgene is maintained. Additional heat is employed to obtain an isothermic reaction zone temperature of 100°C. With a throughput time of 16 seconds, each hour 1,163 grams raw end product are obtained, containing 93% cyclohexyl chloroformate. The yield, based on cyclohexanol, is 86%.

EXAMPLE 8

An hourly feed of 1,383 grams phenyl carbinol with 1,100 grams phosgene is introduced into a reaction zone heated to 170°C. With a throughput time of 17 seconds an hourly raw product output of 1,930.5 grams, containing 91% benzyl chloroformate, is obtained. The yield, based on the phenyl carbinol, is 81%.

We claim:

1. In a process for producing a chloroformate by reaction of an alcohol with gaseous phosgene in a reaction zone the improvement which comprises reacting said alcohol in the atomized state.

2. The process as claimed in claim 1 wherein said reaction gives rise to an atomized phase containing chloroformate produced by the reaction and a vapor phase containing hydrochloric acid produced by the reaction.

3. The process as claimed in claim 2 further including the step of recovering the chloroformate from said atomized phase.

4. The process of claim 3, wherein the chloroformate is recovered by separating same from hydrogen chloride byproduct and any unreacted phosgene.

5. The process of claim 4, wherein said step of separating comprises terminating the atomized state or condensing the components of the reaction mass.

6. The process of claim 5, wherein after said step of separating the temperature of the chloroformate is between 30°C and 60°C.

7. The process of claim 6, wherein said temperature is between 35°C and 45°C.

8. The process as claimed in claim 1 wherein heat of reaction creates an isothermic condition throughout said zone whereby said zone contains substantially no temperature gradient.

9. The process as claimed in claim 1 further including the step of alternatingly increasing then decreasing pressure within said zone to decrease throughput time.

10. The process as claimed in claim 1, wherein the alcohol is atomized by the pressure of the phosgene.

11. The process of claim 1, wherein said alcohol is methanol, ethanol, isopropanol, cetol, ethylene chlorohydrin, β-butoxyhexanol, cyclohexanol, or phenyl carbinol.

12. In a process for producing a chloroformate by reaction of an alcohol with gaseous phosgene in a reaction zone the improvement which comprises, atomizing the alcohol by the vapor pressure of the phosgene; introducing the atomized alcohol and the phosgene into the reaction zone; and coreacting the atomized alcohol with the phosgene substantially immediately upon introduction into said zone, whereby heat of reaction creates an isothermic condition throughout said zone, as a consequence thereof said zone containing substantially no temperature gradient, said isothermic condition shifting the reaction toward the production of chloroformate, increasing the yield thereof and decreasing carbonate byproduct formation.

13. The process as claimed in claim 12 further including the step of recovering the chloroformate from said zone.

* * * * *